United States Patent
Gokhale et al.

(10) Patent No.: US 8,835,660 B2
(45) Date of Patent: Sep. 16, 2014

(54) METHOD FOR EXTRACTING ORGANIC COMPOUNDS FROM AQUEOUS MIXTURES

(75) Inventors: Amit A. Gokhale, El Cerrito, CA (US); Sasisanker Padmanabhan, El Cerrito, CA (US); Christopher Roberge, Lafayette, CA (US)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 0 days.

(21) Appl. No.: 13/818,624

(22) PCT Filed: Aug. 22, 2011

(86) PCT No.: PCT/US2011/048646
§ 371 (c)(1), (2), (4) Date: Jul. 11, 2013

(87) PCT Pub. No.: WO2012/027279
PCT Pub. Date: Mar. 1, 2012

(65) Prior Publication Data
US 2013/0281720 A1    Oct. 24, 2013

Related U.S. Application Data

(60) Provisional application No. 61/376,220, filed on Aug. 23, 2010.

(51) Int. Cl.
| | |
|---|---|
| *C07C 51/48* | (2006.01) |
| *C07D 307/46* | (2006.01) |
| *C07C 29/86* | (2006.01) |
| *C07D 307/48* | (2006.01) |
| *B01D 11/04* | (2006.01) |

(52) U.S. Cl.
CPC .............. *C07C 51/48* (2013.01); *C07D 307/46* (2013.01); *C07C 29/86* (2013.01); *C07D 307/48* (2013.01); *B01D 11/0426* (2013.01)
USPC ......................................................... 549/498

(58) Field of Classification Search
CPC .................................................... B01D 11/0426
USPC ......................................................... 549/498
See application file for complete search history.

(56) References Cited

U.S. PATENT DOCUMENTS

| | | |
|---|---|---|
| 4,559,109 A | 12/1985 | Lee et al. |
| 2009/0023902 A1 | 1/2009 | Frank et al. |
| 2009/0215137 A1 | 8/2009 | Hawkins et al. |

FOREIGN PATENT DOCUMENTS

CN          101386678 A          3/2009

OTHER PUBLICATIONS

International Search Report and Written Opinion received for PCT Patent Application No. PCT/US2011/48646, mailed on Jan. 10, 2012, 10 pages.
International Preliminary Report on Patentability recived for PCT Patent Application No. PCT/US2011/048646, mailed on Mar. 7, 2013, 8 pages.
Office Action Received for Chinese Patent Application No. 201180040561.9, mailed on May 6, 2014, 19 pages (10 pages of English Translation and 9 pages of Official Copy).

*Primary Examiner* — Taofiq A Solola
(74) *Attorney, Agent, or Firm* — Morrison & Foerster LLP (57) ABSTRACT

The invention provides a method to extract organic compounds from aqueous mixtures, using a specially selected organic compound as an extraction liquid. The method can be applied to remove compounds such as acetic acid or ethanol from complex aqueous mixtures, including fermentation reactions or broths, and can be used for in situ extraction of products or by-products from a fermentation reaction. Some suitable extraction liquids for use in these methods include diethylene glycol dibutyl ether, tripropionin, and di(ethylene glycol) diisobutyl ether.

20 Claims, 4 Drawing Sheets

METHOD FOR EXTRACTING ORGANIC COMPOUNDS FROM AQUEOUS MIXTURES

CROSS-REFERENCE TO RELATED APPLICATIONS

This application is a U.S. National Phase patent application of PCT/US2011/048646, filed Aug. 22, 2011, which claims the benefit of U.S. Provisional Patent Application No. 61/376,220, filed Aug. 23, 2010, each of which is hereby incorporated by reference in the present disclosure in its entirety.

TECHNICAL FIELD

This application relates to a method for extracting organic compounds from aqueous mixtures, which provides a non-aqueous solution from which the organic compounds can be easily recovered. The invention provides methods for isolating or purifying organic compounds such as lower aliphatic carboxylic acids, particularly acetic acid; lower alcohols, including ethanol; and certain substituted aromatic compounds such as phenols, furans, and anisoles, by extracting them from aqueous mixtures with a carefully chosen extraction liquid.

BACKGROUND ART

The separation of small, polar organic molecules such as acetic acid from aqueous mixtures can be quite complicated and expensive, especially for dilute aqueous mixtures. For example, to separate acetic acid from water by distillation requires that the lower boiling point water be distilled away before the acetic acid can be recovered.

In addition to acetic acid, other small carboxylic acids (e.g., C3-C6 carboxylic acids, including lactic acid, hydroxybutyric acid, and the like) and lower alcohols like ethanol, isobutanol, and other C3-C6 alcohols, and aromatic compounds such as hydroxymethyl furfural, and vanillin are also often obtained or produced in aqueous mixtures such as fermentation broths or by aqueous processing of plant materials. It is difficult and expensive to separate such organic molecules from their aqueous mixtures.

There thus remains a tremendous need for efficient methods for extracting small, polar organic molecules from aqueous mixtures. There is a particular need for methods that permit easy recovery of fermentation products from aqueous mixtures. The present invention addresses many of these issues.

DISCLOSURE OF THE INVENTION

The present invention provides an effective, energy-efficient liquid-liquid extraction method to separate organic compounds such as aromatic compounds, acetic acid and other lower carboxylic acids, lower alcohols, and various small, polar organics from aqueous mixtures. The methods can be used to remove these organic compounds as a method to clean up the aqueous mixture, or as a method to collect the organic compounds from the aqueous mixture. A primary advantage of this method is the low solubility of water in the extraction liquid, which simplifies removing virtually all of the water from the organic product. Another important advantage of the method for certain applications is the use of solvents having high boiling points and high stability, which enables the user to conveniently separate more volatile organic compounds like acetic acid, ethanol, isobutanol or other low-boiling organics from the extraction liquid by distillation. In addition, even organic compounds present at very low concentrations (e.g., less than 1 wt %) can be extracted from aqueous mixtures by these methods, so they provide a viable way to collect organic compounds that are formed or liberated in an aqueous system, such as fermentation products, and to remove organic compounds efficiently for purposes of cleaning the aqueous layer.

In one aspect, the invention provides methods for separating acetic acid, ethanol, and certain other organic compounds from aqueous mixtures by a simple liquid-liquid extraction process. The methods are applicable to extraction of useful organic compounds from fermentations, for example for production of biofuels from lignocellulosic feedstocks, e.g., using saccharides derived from biomass as a fermentable substrate. The methods can be used to collect or remove organic products from fermentation broths in situ, i.e., without stopping the fermentation process; it can be used advantageously in combination with fed-batch fermentation methods to increase the efficiency of the fermentation, for example, by removing inhibitory products from the fermentation to allow it to proceed more rapidly and completely. The fed-batch methodology enables the fermentation reactions to operate at higher effective concentrations, increasing the output from a given reactor volume; this extraction methodology used in combination with a fed-batch fermentation can prevent product or by-product build-up in the high-concentration fed batch process from inhibiting the reaction.

The extraction methods of the invention use a carefully tailored extraction liquid that is not miscible with water, but is sufficiently polar to extract even small, polar organic compounds with reasonably good efficiency, though they do not appreciably extract saccharides from water. The extraction liquid preferably has a high boiling point, too (e.g., over about 150° C., preferably over 200° C., or over about 240° C.), which facilitates collection of lower-boiling organic compounds from the extraction liquid by distillation. This is beneficial for extracting organic compounds that have a significantly lower boiling point than the chosen extraction liquid, so the extracted organics can be distilled out of the extraction liquid without having to distill away the relatively larger volume of the extraction liquid. This also permits convenient recycling of the extraction liquid.

Suitable solvents for the methods described herein are not the typical organic solvents commonly used for such extractions: they are selected for a combination of properties including high boiling points, water immiscibility, preferably low toxicity to fermentation organisms, high chemical and thermal stability, and their ability to extract various organic compounds, including small, polar organics that have high water solubility, out of an aqueous mixture.

Preferred extraction liquids for use in the methods of the invention have the formula (I) or (II) or (III):

(II)

(III)

wherein each R and R' is independently C3-C5 alkyl, and each R" is independently selected from C3-C5 alkyl and C3-C5 acyl. The alkyl and acyl groups include each isomer unless otherwise indicated. The groups R, R' and R" may be the same or different in any given compound of Formula I, II or III; in some embodiments, all of the R, R' and R" groups in a specific extraction liquid are the same. In some embodiments of the extraction liquids of Formula I or II, each R or R' is n-butyl, t-butyl or isobutyl, and in some embodiments of Formula III, each R" is propionyl (—C(=O)CH$_2$CH$_3$; commonly called tripropionin). The method can use a mixture of two or more of these extraction liquids, but frequently the extraction liquid consists largely of one of these compounds, or of a mixture of isomers of one such compound. In some embodiments, the extraction liquid consists essentially of one compound selected from the compounds of Formulas I, II and III. One example of the method uses diethylene glycol dibutyl ether (DEB), or diethylene glycol di-isobutyl ether, or tripropionin, to extract a small, polar organic such as ethanol, isobutanol or acetic acid from an aqueous mixture such as a fermentation broth.

The methods of the invention comprise contacting an aqueous mixture containing at least one organic compound to be extracted with an extraction liquid as described herein, thereby forming a biphasic mixture having an aqueous phase and an organic phase. The biphasic mixture may be mixed, blended, or agitated by any convenient method to accelerate migration of the organic compound(s) to be extracted from the aqueous phase into the organic phase, but active mixing is not required: the organic compound(s) to be extracted will at least partially migrate passively from the aqueous phase into the organic phase. Moreover, in some embodiments, it is preferable to avoid agitation or mixing; for example, where the aqueous mixture has a higher density than the extraction liquid, a layer of an extraction liquid can flow over the top surface of the aqueous mixture, and extractable organic compounds can migrate by passive diffusion into the extraction liquid layer without causing the two layers to mix. At least a portion of the organic phase is then separated from the aqueous phase, thereby taking with it at least some of the organic compound extracted from the aqueous phase.

Methods for using this extraction can utilize any suitable extraction format. It can be done as a batch extraction, which involves adding the extraction liquid to an aqueous mixture, optionally mixing or blending the biphasic mixture, and then separating essentially all of the organic phase from the aqueous phase, and optionally repeating with another aliquot of the extraction liquid It can be done as a continuous extraction, wherein, for example, an extraction liquid is added continuously or in portions to an aqueous mixture such as a fermentation mixture, under conditions where the organic phase forms a localized pool that can be removed continuously or in portions. It can be done as a co-current, cross current or countercurrent extraction; in some embodiments, it is performed as a countercurrent separation, where the organic phase and aqueous phase move in different directions while in contact, typically in opposite directions. It can be done as a multistage countercurrent continuous extraction process, and optionally centrifugation may be used to facilitate phase separation.

The methods can optionally include a step of recovering a portion of the extracted organic compound(s) from the extraction liquid after it has been extracted from the aqueous mixture into the extraction liquid. Methods for this recovery of the organic compounds are well-known in the art. If a low-boiling organic compound is to be isolated, for example, it can be distilled out of the extraction liquid, leaving the higher-boiling extraction liquid behind. If an acidic compound is to be isolated, it can be removed by base extraction, or precipitated as a salt. If a small compound is to be isolated, it can be removed by membrane separation. Various other options and combinations of such methods can be used.

Once the extracted organic compound(s) have been recovered or removed from the extraction liquid, the extraction liquid can optionally be recycled or reused.

Organic compounds to be extracted include any suitable organic compound present in the aqueous mixture. Among these, certain aromatic compounds, polar compounds, alcohols, amines, carboxylic acids, esters, and amides are of special interest. Small, polar organics are particularly important, because they are often produced in or extracted with aqueous media, and are difficult to remove from or recover from the aqueous media. Examples of organic compounds that can be extracted from an aqueous mixture by the methods of the invention include C2-C6 alcohols, C2-C6 carboxylic acids, C2-C6 ketones and aldehydes, and substituted aromatics such as phenols, benzoic acids, salicylates, vanillin, furans, furfural, hydroxymethylfuran, and 5-hydroxymethylfurfural. In many embodiments, the compound to be extracted is one or more C2-C4 alcohols or C2-C4 carboxylic acids or a C2-C6 ketone. Of special importance are acetic acid, ethanol, and isobutanol, which are difficult to recover by conventional methods but can be extracted and recovered efficiently by the above-described methods; for example, they can be extracted from a fermentation mixture or similar growth medium where they are being produced. In some embodiments, these products of fermentation are extracted in situ, i.e., from an active fermentation mixture without disrupting the fermentation process, such as by using a continuous extraction process that contacts the operating fermentation mixture with a suitable extraction liquid to remove products or by-products of fermentation without stopping the fermentation reaction.

One embodiment of the invention includes use of DEB to extract acetic acid and/or ethanol from an aqueous mixture such as a fermentation process.

In one aspect, the invention provides a method to extract one or more organic compounds from an aqueous mixture, comprising contacting the aqueous mixture with an extraction liquid of Formula I, II or III:

wherein each R and R' is independently C3-C5 alkyl, and each R" is independently selected from C3-C5 alkyl and C3-C5 acyl, to produce a biphasic composition; and separating at least a portion of the extraction liquid phase from the aqueous phase to provide an extract solution comprising the organic compound.

In some embodiments, the organic compound is a small, polar organic compound. It can be an aromatic compound such as a C5-C10 aryl or heteroaryl having at least one heteroatom in the ring or in a substituent on the ring. It can be a C2-C6 monohydric alcohol, a C2-C6 carboxylic acid, or a C2-C6 aldehyde or ketone. In some embodiments, the organic compound is selected from acetic acid, propionic acid, butyric acid, valeric acid, hexanoic acid, hydroxypropionic acid, hydroxybutyric acid, ethanol, propanol, isopropanol, 1-butanol, 2-butanol, isobutanol, t-butanol, 1-pentanol, 2-pentanol, 2-methyl-2-pentanol, 1-hexanol, 2-hexanol, and 2-methyl-2-pentanol. In certain embodiments, the organic compound is ethanol, isobutanol, or acetic acid. In certain embodiments, the organic compound is acetic acid, and the acetic acid is extracted from the aqueous mixture with a distribution coefficient of about 0.5 to about 1.0. In certain embodiments, the organic compound is ethanol, and the ethanol is extracted from the aqueous mixture with a distribution coefficient of about 0.8 to about 1.4. In certain embodiments, the organic compound is isobutanol, and the isobutanol is extracted from the aqueous mixture with a distribution coefficient of about 2.3 to about 4.1. In certain embodiments, the organic compound is hydroxymethylfurfural. In certain embodiments, the organic compound is hydroxymethylfurfural, and the hydroxymethylfurfural is extracted from the aqueous mixture with a distribution coefficient of about 0.4 to about 0.7. In certain embodiments, the organic compound is furfural. In certain embodiments, the organic compound is furfural, and the furfural is extracted from the aqueous mixture with a distribution coefficient of about 0.8 to about 1.2.

In some embodiments, the method further comprises a step wherein at least a portion of the organic compound is separated from the extract solution comprising the organic compound. The organic compound can be recovered for use. Removal of the organic compound facilitates recycling and reuse of the extraction liquid.

In some embodiments, the extraction liquid phase and aqueous phase of the biphasic composition are mechanically mixed before the extraction liquid phase is separated from the aqueous phase. This can be done by any convenient method that facilitates migration of the organic compound from the aqueous phase into the extraction liquid phase. The phases may then be allowed to stand, if necessary, before separation. Other manipulations like filtration may also be included as appropriate.

The method can be performed using any convenient format. In some embodiments, the method is performed as a batch extraction. In other embodiments, it is performed as a continuous extraction method. The method can be used for a co current, counter-current or cross-current continuous extraction process.

The method may be applied to any suitable aqueous mixture. In some embodiments, it is used to recover organic compounds from a fermentation mixture, either by extraction of the active fermentation reaction (in situ extraction), or by extraction of a broth from a fermentation reaction, or by extraction of a partially-processed fermentation broth, which may have already undergone filtration, centrifugation, decolorization, heat treatment or other manipulations. Of special interest is use of the methods described herein for in situ extraction of an active fermentation reaction mixture. This can be used to accelerate or sustain the fermentation reaction rate, by removing fermentation products such as acetic acid or ethanol that can inhibit fermentation as they are produced. It can be used with batch or fed-batch fermentation processes to promote more efficient utilization of fermentation equipment and of saccharide inputs for the fermentation.

The methods may be practiced at any convenient operating temperature; typically between the freezing and boiling points of the aqueous mixture. In some embodiments, the step of contacting the aqueous mixture with an extraction liquid of Formula I, II or III to produce a biphasic mixture is performed at a temperature above about 30° C. This can be done with a fermentation reaction, and is particularly useful when used for a fermentation that is operated at an elevated temperature, such as when using a thermophilic fermentation organism.

In another aspect, the invention provides a method to remove at least a portion of a particular organic compound such as acetic acid or ethanol from an aqueous mixture by contacting the aqueous mixture with a first portion of an extraction liquid of Formula I, II or III to form a biphasic mixture having an aqueous phase and a first extraction liquid phase, whereby at least a portion of the organic compound (e.g., acetic acid or ethanol) migrates from the aqueous liquid into the first extraction liquid phase, then separating at least a portion of the first extraction liquid phase from the biphasic mixture.

Optionally, most or all of the first extraction liquid phase can be separated from the aqueous phase. This can be done as a batch process, and the extraction step can be repeated as appropriate. Alternatively, this can be performed in a continuous-extraction mode, too, where an amount of the extraction liquid remains continuously in contact with the aqueous mixture throughout the process. The amount of extraction liquid remaining in contact with the aqueous mixture can be from about 1% of the volume of the aqueous mixture to about 100% or more of the volume of the aqueous mixture.

This method also optionally comprises recovering at least a portion of the organic compound (e.g., acetic acid or ethanol) from the extraction liquid phase.

This method can be performed at any convenient pH. In some embodiments, a pH of up to about 9 is used. Where the organic compound is a carboxylic acid, a pH of about 7 or less and preferably of about 6 or less or about 5 or less is typically used.

The method can be performed to remove any appropriate amount of the organic compound, depending upon the purpose of the extraction. Where the extraction is used to prevent build-up of toxic products or by-products in a fermentation reaction, for example, the amount removed may be an amount sufficient to facilitate continued fermentation. Where it is used to recover the organic compound, the extraction may be repeated in batch mode, or continued in a continuous-extraction mode, until at least about 50% and preferably 60% or more of the organic compound is removed from the aqueous mixture.

In another aspect, the invention provides a continuous process for extracting an organic compound from an aqueous mixture, that involves contacting the aqueous mixture with an extraction liquid of Formula I, II or III, to form a biphasic composition comprising an aqueous phase and an extraction liquid phase; maintaining the extraction liquid phase in contact with the aqueous phase for a residence time to allow at least some of the organic compound to migrate into the extraction liquid phase to form an extraction liquid phase containing some of the organic compound; adding more extraction liquid to the extraction liquid phase containing the organic compound or to the aqueous phase while the extraction liquid phase containing the organic compound and the aqueous phase remain in contact with each other, while concurrently removing a portion of the extraction liquid phase containing the organic compound from the biphasic composition while the extraction liquid phase containing the organic compound and the aqueous phase remain in contact with each other.

Any suitable residence time can be used; selecting a suitable residence time is routine for a given system, depending upon volumes of material, operating conditions and partitioning coefficients of the organic compound(s) involved.

This continuous process can be used with a fermentation broth or for in situ treatment of an operating fermentation reaction, or with an enzymatic reaction. It can be used to remove by-products from an enzymatic reaction or fermentation process that inhibit reaction progress. For example, it can be used to remove ethanol or acetic acid building up in a fermentation reaction, to promote further and/or faster fermentation reaction progress.

In another aspect, the invention provides a method to convert biomass into acetic acid and/or ethanol. This method may require pretreating biomass to release saccharides (mono-, di- and/or oligo-saccharides) from biomass for fermentation. Saccharides derived from biomass are then brought into contact with a fermenting microorganism in an aqueous carrier to provide a fermentation mixture. The fermentation mixture is maintained under suitable fermentation conditions to permit desired products, e.g., acetic acid and/or ethanol to form in the fermentation mixture. The fermentation mixture is then contacted with an extraction liquid to form a biphasic composition having an aqueous carrier phase and an extraction liquid phase, thereby extracting at least a portion of the desired product, e.g. acetic acid and/or ethanol, from the aqueous carrier phase into the extraction liquid phase. Experimental data provided herein demonstrate that this can be achieved with suitable extraction liquids such as a compound of formula I, II or III:

wherein each R and R' is independently C3-C5 alkyl, and each R" is independently selected from C3-C5 alkyl and C3-C5 acyl.

Typically, the extraction liquid will be used in an amount at least 1% of the volume of the aqueous mixture, preferably at least about 10%. In some embodiments, the volume of extraction liquid will be over about 25% of the volume of the aqueous mixture, often at least 50% of the volume of the aqueous mixture, and in some embodiments, 100% or more of the volume of the aqueous mixture. This volume of the extraction liquid may be used in a single batch extraction, or it may be used in smaller portions for multiple batch extractions, or it may be used in a continuous extraction format.

The method can further include a step of separating a portion of the extraction liquid phase containing acetic acid and/or ethanol from the aqueous carrier phase. As further described herein, the desired product (acetic acid and/or ethanol, for example) can be recovered from the extraction liquid phase, and the extraction liquid can be recovered for re-use. This can be applied to in situ extraction of ethanol or acetic acid from a fermentation reaction.

In another aspect, the invention provides a method to produce transportation fuel, particularly a method to produce bio-fuel from biomass, comprising a step of extracting an organic compound from an aqueous mixture using any of the methods discussed herein. The transportation fuel includes hydrocarbons and oxygenated hydrocarbons that are liquid at ambient temperature and have two or more carbon atoms; examples include ethanol, MTBE, isomers of butanol, and the like. In some embodiments, the method includes fermentation to convert saccharides from biomass into organic compounds described herein, such as acetic acid, ethanol, butanol, or isobutanol, and the extraction methods discussed herein are used to recover the organic compounds from an aqueous mixture derived from the fermentation process.

Suitable extraction liquids for any of the above aspects and embodiments of the invention include compounds of Formula I, particularly those compounds wherein the R groups are the same. In some preferred embodiments, the R groups are butyl groups. Specific preferred extraction liquids include diethylene glycol dibutyl ether (DEB) or diethylene glycol diisobutyl ether.

Other suitable extraction liquids are compounds of Formula II as described above, particularly those compounds wherein the R groups are the same. In some preferred embodiments, the R groups are butyl groups.

Other suitable extraction liquids for any of the foregoing aspects and embodiments of the invention are compounds of Formula III. One preferred extraction liquid of this formula that is particularly advantageous for operating at temperatures above ambient is called tripropionin.

It will be understood that variations and combinations of the features of the above-described aspects and embodiments are also included in the scope of the invention.

Other aspects and embodiments of the invention are set forth below along with working examples and experimental results, from which a person of ordinary skill can practice the invention described herein.

MODES OF CARRYING OUT THE INVENTION

Liquid-liquid extraction is one of the simplest methods to remove an organic compound from an aqueous mixture, whether the removal is done to reduce the amount of the organic compound in the aqueous mixture or to collect the organic mixture from a spent aqueous mixture. Liquid-liquid extraction is commonly used to extract relatively lipophilic compounds from water; lipophilic compounds have low affinity for water, and are readily extracted into a more compatible medium like a typical organic solvent. However, its use for small, highly polar organic compounds is complicated by several factors. First, a highly polar organic compound may have high water solubility, and thus be very difficult to extract into organic solvents that are lipophilic enough to be immiscible with water, and of course organic solvents like acetone or ethanol that are miscible with water cannot be used for such extractions under normal conditions because they mix with water rather than forming two separable phases.

Polar organic solvents like n-butanol are sometimes able to extract a highly polar compound from water, but typically these solvents have significant miscibility with water. They form biphasic mixtures, but often a significant amount of the organic solvent is lost into the aqueous phase, and the polar organic phase is typically 'wet'. Thus while some extraction of the polar organic compound is achieved, the organic solvent layer containing the extracted polar compound may contain a large amount of water that needs to be removed. Moreover, significant amounts of the organic solvent are lost, making it harder to recycle the solvent; and the disposal or treatment of the aqueous stream is complicated by the presence of the organic solvent. In addition, butanol and similar polar organic solvents can be difficult to efficiently separate from the polar compound being extracted, particularly if the compound to be extracted is similar in molecular weight and polarity to the extraction solvent. Thus, while liquid-liquid extraction can be very useful for separating organic compounds from water, it can be quite difficult to find an ideal solvent for a particular separation, and ideal solvents for extraction of small, polar organics from aqueous mixtures that work well in large-scale processing are needed.

After a great deal of experimentation, the inventors found a particular class of extraction liquids that can be used as a solvent for extracting acetic acid, ethanol, and other organic compounds from aqueous mixtures. They found that compounds of Formula I, II and III as described herein are effective extraction liquids for this purpose, and have other desirable properties such as relatively high boiling points, low water solubility, and low tendency to extract water, as well. These properties make them particularly useful for liquid-liquid extraction of organic compounds from aqueous mixtures.

Extraction liquids within the scope of the invention include compounds of formula (I) where each R group is a C3-C5 alkyl, which may be the same or different. In some embodiments, each R is selected from propyl, isopropyl, n-butyl, iso-butyl, t-butyl, pentyl, 2-pentyl, neopentyl, and 3-pentyl. In some embodiments, the two R groups are the same, and in some instances, a C4 group, e.g., n-butyl, t-butyl, isobutyl, or sec-butyl, is preferred.

Other extraction liquids within the scope of the invention include compounds of Formula (II) where each R', which may be the same or different, is selected from C3-C5 alkyl. In some embodiments, each R' is the same, and is selected from propyl, isopropyl, n-butyl, sec-butyl, isobutyl, t-butyl, pentyl, 2-pentyl, neopentyl, and 3-pentyl. In some embodiments, the two R groups are the same, and in some instances, a C3 or C4 group is preferred, e.g., n-propyl, isopropyl, n-butyl, sec-butyl, or isobutyl.

Other extraction liquids within the scope of the invention include compounds of Formula (III) where each R" is C3-C5 alkyl or C3-C5 acyl. In some embodiments, the R" groups are all the same, and are selected from propyl, butyl, pentyl, t-butyl, isobutyl, isopropyl, 3-pentyl, propionyl, isobutyryl, butanoyl, pentanoyl, and pivaloyl. In some embodiments, the three R groups are the same, and in some instances, butyl, propyl, or propionyl is preferred.

Organic compounds to be extracted by the methods described herein include any suitable organic compound present in an aqueous mixture. Among these, certain aromatic compounds, polar compounds, alcohols, amines, carboxylic acids, esters, and amides are of special interest. Small, polar organics are particularly important, because they are often produced in or extracted with aqueous media, and are difficult to remove from or recover from the aqueous media. Examples of organic compounds that can be extracted from an aqueous mixture by the methods of the invention include C2-C6 alcohols, C2-C6 carboxylic acids, C2-C6 ketones and aldehydes, and substituted aromatics such as phenols, benzoic acids, salicylates, vanillin, furans, furfural, hydroxymethylfuran, and 5-hydroxymethylfurfural. In many embodiments, the compound to be extracted is one or more C2-C4 alcohols or C2-C4 carboxylic acids or a C3-C6 ketone. Of special importance are acetic acid, ethanol, and isobutanol.

Aqueous mixtures useful in the invention include any mixture containing or consisting at least partly of an aqueous solution or suspension. These include aqueous extracts of biological, petrochemical, or mineral products, and fermentation broths, both live (in operation) and at various processing stages. The methods are particularly useful for in situ extraction of fermentation broths or enzymatic reactions during operation, i.e., extraction of organic compounds performed while the fermentation is ongoing, or while an enzymatic reaction is occurring, without interrupting the fermentation or enzymatic reaction.

The methods of the invention involve forming a biphasic mixture having an aqueous phase and an organic phase comprising the extraction liquid, which may remain in contact for a suitable period of time, referred to as residence time. A suitable residence time for a particular extraction process can be determined by routine experimentation.

While the methods of the invention can be practiced at any suitable temperature and pressure, including ambient temperature and pressure, it is sometimes advantageous to perform an extraction with one of the extraction liquids of the invention at an elevated temperature, e.g., at a temperature above 30° C., or above 40° C., or above 50° C., or above 60° C. For example, tripropionin (a compound of Formula III, where each R" is propionyl) provides satisfactory extraction of ethanol at ambient temperature; but at higher temperatures, e.g., 60-65° C., it performs better, having improved partitioning properties. Computational results described herein (see Tables 4-8) illustrate why the extraction liquids perform better at elevated temperatures.

One example of the method uses diethylene glycol dibutyl ether (DEB). Computational modeling using the parameters and methods described herein suggest that diethylene glycol diisobutyl ether (DIBE) will perform even better. DEB is not miscible with water, so contacting an aqueous mixture with DEB produces two separate and readily separable phases. Even though it is not miscible with water, DEB nevertheless is polar enough to extract significant proportions of small, polar organic compounds from water. In this example, the invention takes advantage of the discovery that significant fractions of acetic acid, ethanol and isobutanol migrate from an aqueous phase into DEB when permitted to do so. These small, polar organic products can thus be extracted with DEB from aqueous mixtures, including complex mixtures like a fermentation broth. The invention thus provides methods for at least partially removing organic compounds from an aqueous phase when it is desirable to reduce their presence in the aqueous phase, and methods for recovering these organic compounds from an aqueous phase. It also provides methods for using this extraction process to collect these compounds from a fermentation mixture, even while the fermentation process continues to operate, because the DEB has very low solubility in water and does not typically interfere with fermentation.

The extraction methods of the invention can be practiced by conventional methods and apparatus well known in the art for liquid-liquid extractions. The apparatus typically provides for contacting an aqueous mixture that contains a small, polar organic compound of interest with an extraction liquid of the invention for a sufficient period of time to permit a portion of the small, polar organic compound to partition into the extraction liquid. Frequently, mixing or agitation is performed to promote mixing of the aqueous mixture with the extraction liquid. Once a portion of the small, polar organic compound has partitioned into the extraction liquid phase, a portion of the extraction liquid phase (usually most or virtually all of it) is separated from the aqueous mixture, leaving the aqueous mixture depleted in the small, polar organic compound, and providing a solution of the extraction liquid that contains some of the small, polar organic compound. This process is repeated or continued until the desired extraction effect is achieved.

The extraction methods of the invention can be practiced by 'batch' extraction, or by a continuous extraction process. The methods often use an amount of the extraction liquid that is at least about 1% of the volume of the aqueous mixture, often at least about 10% of the volume of the aqueous mixture, typically at least about 50% of the volume of the aqueous mixture, and optionally about 100% or more of the volume of the aqueous mixture. The amount used can be used in a single-pass extraction, or it can be used in multiple portions. The partitioning of an organic compound between the aqueous phase and the extraction liquid phase can readily be determined by simple experiments, and this information can be used to determine how much of the extraction liquid is appropriate to use for a particular polar organic compound to be extracted and when the desired extraction effect has been achieved.

Figure 1:
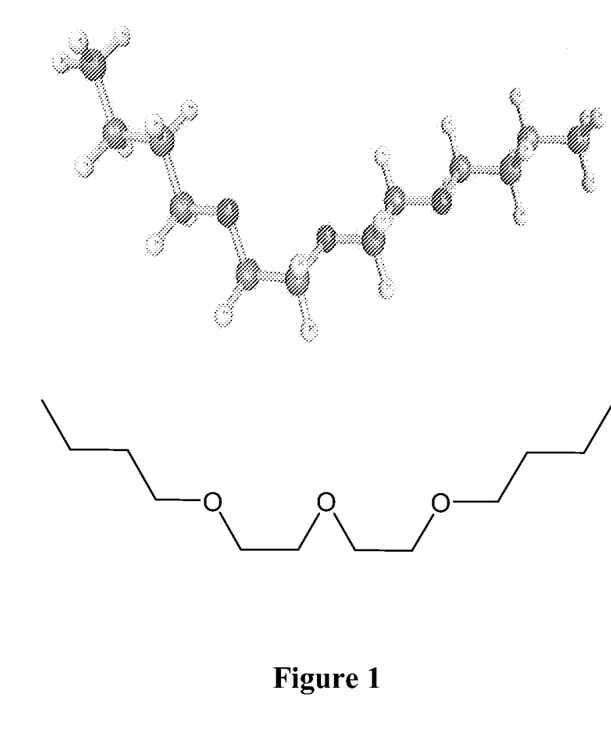
FIG. 1 shows the chemical structure of DEB, an example of a suitable extraction liquid, and depicts one conformation of DEB.

Diethylene glycol dibutyl ether (DEB; see FIG. 1) is an example of a suitable extraction liquid: DEB was found to have an excellent balance of polarity, water immiscibility, and other properties to extract the targeted compounds from water with good efficiency, and to produce an extract that is relatively low in water. While not among the conventional solvents for such extractions, it is reasonably economical to produce and use, has good safety/toxicity properties, and as discussed herein, it can be recycled and reused readily. As an additional benefit, its boiling point is relatively high, and as a result, acetic acid and many of the small, polar organic compounds of interest can be distilled out of DEB readily, so the compounds extracted into DEB can be efficiently recovered, and the DEB can be recycled and reused. Alternatively, small carboxylic acids extracted by the methods of the invention can easily be removed from the DEB extract by a base extraction, permitting rapid and simple recycling or reuse of the DEB.

Acetic acid can be recovered from the DEB extracts by distillation, or it can be removed by basic aqueous extraction. Separation by distillation is easy, because acetic acid has a boiling point of 118° C., while DEB boils at 256° C. (1 atm). Because DEB can be reused readily, this novel acetic acid extraction process produces little waste; and distilling acetic acid out of DEB takes much less energy than distilling it from a crude fermentation broth. Thus this process is significantly more efficient and environmentally friendly than prior methods for removing acetic acid from complex aqueous mixtures such as fermentation broths. The present methods thus provide an environmentally friendly method for removing acetic acid from aqueous mixtures.

Acetic acid was found to partition between water and DEB about equally, i.e., its partition coefficient (concentration of acetic acid in DEB/concentration of acetic acid in water) at room temperature is about 1. Thus by using a volume of DEB that is about equal to the volume of water, about half of the acetic acid can be extracted from water in a single extraction. Because acetic acid can be easily removed from DEB, the DEB can be recycled and thus can be used for multiple extractions. By using repeated extractions, this provides a simple method to extract acetic acid from water and thus lower the acetic acid concentration in the aqueous layer to any desired level.

In addition to its ability to extract acetic acid, DEB has been found to be effective for extracting other small, polar organic compounds from aqueous media, too. In particular, C2-C6 carboxylic acids, ethanol, and C3-C6 mono-hydric alcohols can be separated from water efficiently using DEB as an extraction solvent; and they can be easily recovered from DEB using simple distillation or base extraction methods.

One important attribute of the extraction liquids of the invention such as DEB is the low solubility of water in extraction liquid. The extraction liquids of Formula I, II and III form immiscible layers when mixed with water that are relatively easy to separate, and each layer has quite low solubility in the other. Experiments indicate that when DEB is saturated with water under standard conditions (room temperature, 1 atm.), for example, it contains about 300 ppm water, or about 0.3 g water per kg of DEB. As a result, a simple extraction process provides acetic acid with low water content, so little energy is wasted separating acetic acid from remaining water.

Another important attribute of extraction liquid of Formulas I, II and III are their low solubility in water; as described herein, DEB, for example, appears to have water solubility less than about 10 ppm. Thus when used to extract small, polar organics from water, very little of the extraction liquid partitions into the aqueous phase. This simplifies recovery of the small, polar organic compound and reduces possible losses of the extraction liquid in the aqueous phase.

Like most of the extraction liquids of Formulas I, II and III, DEB is less dense than water (d=0.885 in literature). When using an extraction liquid to extract small, polar organics from an aqueous solution, the extraction liquid phase is also slightly less dense than the aqueous solution. Contacting the aqueous solution with extraction liquid produces two phases, and the extraction liquid phase is less dense than the aqueous phase even after some extracted organic compound(s) migrates out of the aqueous solution and into the extraction liquid phase. The upper layer of the biphasic mixture of extraction liquid plus an aqueous solution is thus the extraction liquid phase.

Another important attribute is the ability of DEB to extract lower alcohols from aqueous mixtures instead of or in addition to carboxylic acids like acetic acid. Ethanol and isobutanol can be produced in fermentation reactions, for example, and they can be recovered from an aqueous mixture by DEB extraction. They, too, can be easily separated by distillation from DEB: ethanol boils at 79° C., and isobutanol boils at 108° C. This means that DEB extraction is useful for extraction of isobutanol, ethanol and acetic acid from fermentation broths, enabling more complete utilization of feedstocks and more efficient recovery of products from fermentation reactions. An in situ DEB extraction would reduce the concentration of products of fermentation as well as inhibitors of fermentation, effectively driving the reaction forward toward more complete conversion. In addition to stopping fermentation, the accumulation of fermentation products in batch fermentations often results in metabolic changes that cause increased formation of other byproducts in response to the stress, and hence lower yields, rates, and/or efficiency. The extraction described herein can significantly reduce those stresses and increase yields.

This method can also support use of microorganisms that are highly productive for fermentation but which are not very tolerant of reaction products, and are thus not efficient in batch production because fermentation stops too early due to product inhibition. Use of the extraction methods described herein permits removal of products without interrupting the fermentation process or having to re-start the fermentation reaction or recycle incompletely-consumed feedstock. Extraction of small, polar organic products from active fermentation reactions can thereby be used to produce more efficient fermentation. It can even enable use of ethanol-sensitive or acetic acid (pH)-sensitive strains of fermenting organisms by avoiding build-up of ethanol or acetic acid in a fermentation reaction. Moreover, the finding that the extraction methods operate better at slightly elevated temperatures enables use of fermentation organisms that function better at elevated temperatures, in the range of 30-40° C.; 40-50° C.; 50-60° C.; or 60-70° C.

The methods of the invention are generally applicable to most aqueous mixtures that contain the small, polar organic compounds contemplated herein. Concentrations as low as 1% acetic acid have been shown to permit reasonably efficient extraction of acetic acid with DEB. Higher concentrations work well also, up to about the saturation point for acetic acid in DEB, which is about 30% acetic acid. Theoretical considerations indicate that miscibility of water and DEB should decrease as temperature increases. The extraction methods are thus expected to be useful across a temperature range covering most of the temperature range where water is liquid at atmospheric pressure.

For the methods of the invention to operate on C2-C6 carboxylic acids, the aqueous mixture generally needs to be acidic enough for the carboxylic acids to be at least substantially protonated, so typically the aqueous mixture should have a pH of up to about 9, and optionally a pH of about 6 or less, or about 5 or less. For an aqueous solution having a higher pH, it may be necessary to first acidify the aqueous layer before using the methods of the invention. For use in extracting carboxylic acids from a fermentation reaction, the reaction needs to operate at a pH of about 6 or lower; this obviously is not a limitation if the methods are used to extract alcohols or most other small, polar organics, which will not be extensively ionized at pH levels up to at least about 14. This also enables the user to extract alcohols from an aqueous mixture without extracting carboxylic acids, by merely adjusting the pH of the aqueous mixture to a basic pH, e.g, about 8 or above. For extraction of phenols, a pH up to about 10 or 12 may be suitable depending upon the pKa of the phenol; selection of a suitable pH can be determined where necessary by reference to the pKa of the compound to be extracted. Typically the pH of the aqueous mixture to be extracted should be about equal to or lower than the pKa of an organic compound to be extracted.

Extraction of acetic acid from an aqueous mixture into an extraction liquid involves contacting the aqueous mixture with sufficient extraction liquid to remove a desired amount of acetic acid. The amount of acetic acid that can be removed depends largely upon the relative volumes of the aqueous mixture and the added extraction liquid: acetic acid distributes between water and extraction liquid with a distribution coefficient of about 1. Thus if equal volumes of aqueous mixture and extraction liquid are used, about half of the acetic acid will migrate into the extraction liquid phase when equilibrium is reached.

In order to maximize the amount of a small, polar organic compound removed from an aqueous mixture by a given amount of extraction liquid, sufficient contact time (residence time) should be allowed for the acetic acid to substantially equilibrate between the two layers. Because the targeted organic starts out in the aqueous layer, if the extraction liquid layer is separated from the aqueous layer before equilibrium is reached, the maximum amount of small, polar organic compound will not be extracted into the extraction liquid.

While the targeted organics will naturally migrate from water into extraction liquid until equilibrium is reached whenever the layers are in contact, it is sometimes preferable to actively promote migration of the targeted organic(s) into extraction liquid by mechanically mixing the aqueous mixture and extraction liquid phases. This can be done by any conventional mixing means, such as stiffing, vortexing, blending, inverting the container to force the layers to mix, and various methods of injecting one layer, preferably in the form of droplets, into the other layer. Such mixing increases the rate at which the polar organic compound migrates into the extraction liquid layer. Such mechanical mixing can be used in a 'batch' extraction process or in a continuous extraction process.

Figure 2:
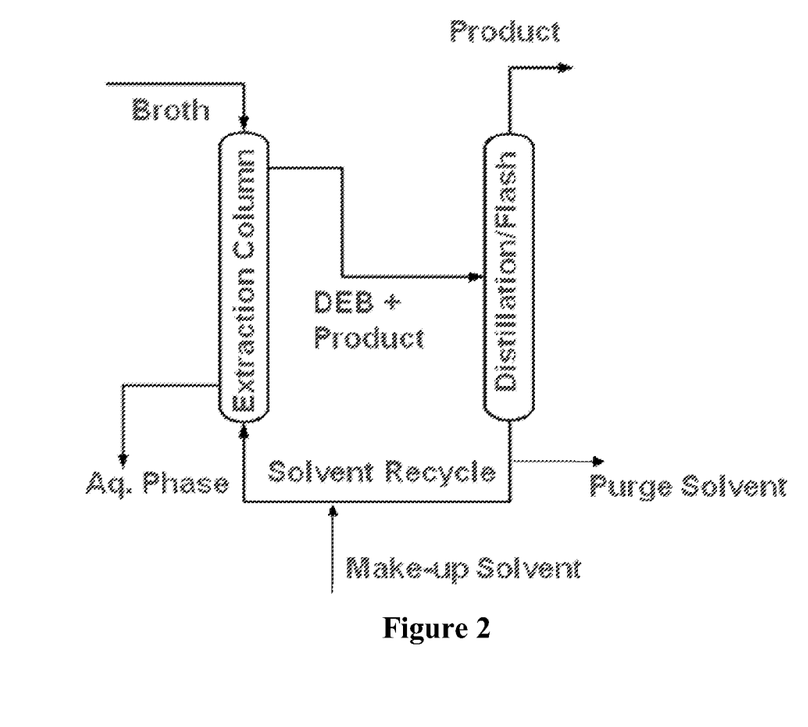
FIG. 2 shows a diagram of an extraction column using the methods of the invention, including recycling DEB.

FIG. 2 depicts one system for using the current methods in a 'batch' process; other configurations are of course possible. A fermentation broth is fed into an extraction column, which uses extraction liquid to extract product from the broth. The extraction liquid phase containing product is directed to a separation module (column or distillation apparatus), where product is removed from the extraction liquid and collected. The extraction liquid is then recycled into the extraction column.

For a continuous extraction especially, another method to accelerate the extraction process is to deliver the extraction liquid directly into the aqueous mixture, so it must pass through the aqueous mixture before joining the less-dense organic (extraction liquid) phase. If extraction liquid is thus injected into the aqueous mixture so that it forms droplets dispersed within the aqueous mixture, migration of polar organics into the extraction liquid phase can occur more quickly.

Figure 3:
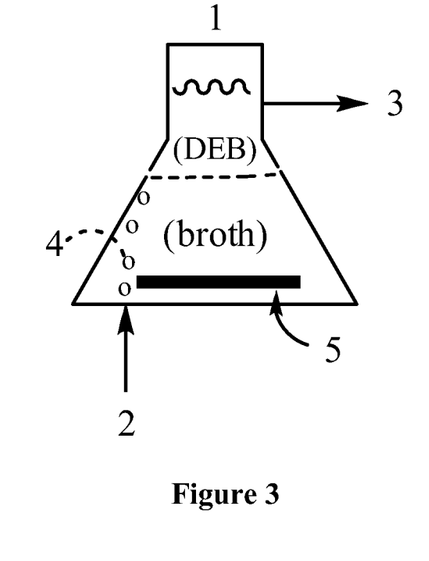
FIG. 3 shows a diagram of in situ continuous extraction of a fermentation broth using the methods of the invention.

FIG. 3 depicts a continuous extraction process using the methods described herein. A reaction container (1) contains an active fermentation broth, with a layer of extraction liquid on top. Extraction liquid is added at the bottom of the container by an extraction liquid inlet (2), and can exit from the extraction liquid layer on top via an overflow/outlet (3). Extraction liquid is added via the inlet, and droplets (4) of extraction liquid move upward through the broth, thereby extracting small, polar organic compounds from the broth. Because the solubility of extraction liquid in water is low, and extraction liquid is not very toxic, it does not interfere with the fermentation process as long as appropriate conditions are maintained in the broth. Optionally, a mechanical stirring device (5) is also used to agitate the broth, facilitating both fermentation and mixing/extraction by extraction liquid.

The methods of the invention can be used to extract products such as ethanol or acetic acid from any aqueous-based fermentation mixture. Suitable fermentation mixtures include those wherein a fermenting organism is contacted with a carbon source such as various biomass materials, e.g., saccharides (mono-, di-, and/or oligosaccharides), derived from various starchy or cellulosic starting materials, including suitably preprocessed biomass. Examples include mono/disaccharides, and biomass materials such as cane, beets, fruits, corn, and the like, as well as any lignin-rich and/or cellulose-rich plant material (switchgrass, wood chips, etc.) that is readily utilized as a carbon source by the fermenting organism. The biomass may be pre-treated to release fermentable mono-, di- and/or oligo-saccharides prior to the fermentation step. The fermentation mixture is maintained under suitable conditions to promote consumption of the biomass by the fermenting organism; conditions for maintaining such fermentation reactions are well-known in the art.

As discussed above, this method is an efficient way to collect acetic acid, or to remove it from an aqueous mixture. It accomplishes this with a distribution between extraction liquid and water of about 1 (measured value for DEB), i.e., at equilibrium, the concentration of acetic acid in the aqueous phase of a DEB extraction mixture is about the same as the concentration in the DEB phase.

Figure 4:
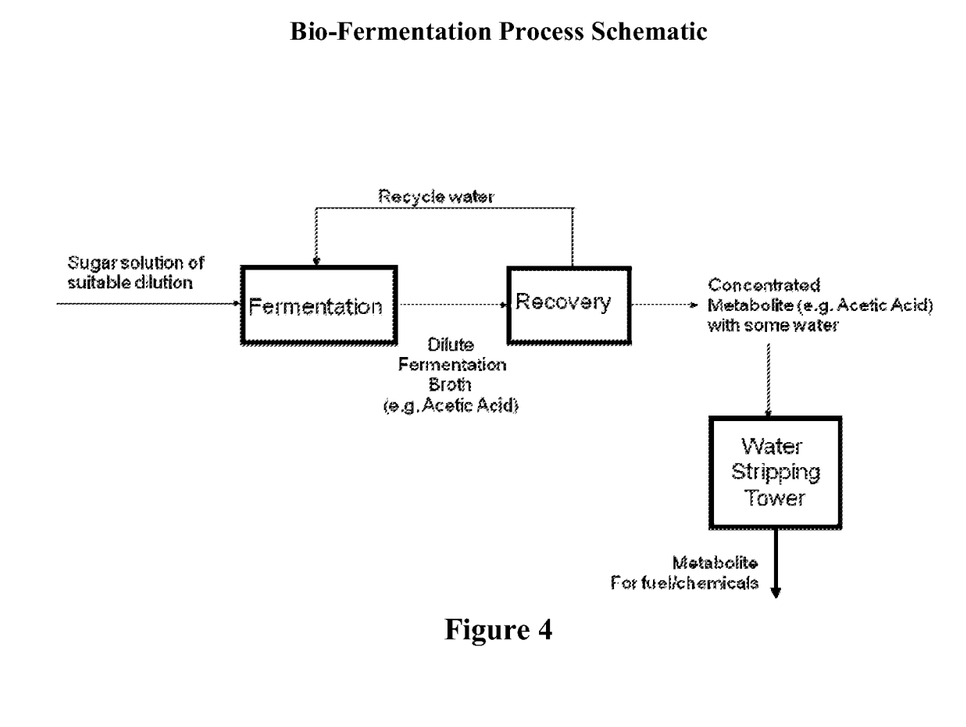
FIG. 4 shows use of the current invention in a process diagram for use in a fermentation process.

FIG. 4 is a schematic diagram for an acetic acid production process using extraction liquid to extract product from the broth. It uses an acetogenic bacterium to produce acetic acid as a major product from oligosaccharide inputs, and DEB or other extraction liquids described herein can be used to remove acetic acid from the culture medium without interrupting fermentation/acetic acid production. Methods for culturing the acetogenic bacteria to produce acetic acid are well known; suitable acetogenic organisms may include, for example, *Sporomusa silvacetica, Moorella thermoacetica, Clostridium magnum, Acetobacterium woodii*, and others.

It was also found that the distribution of ethanol between water and DEB is similar; thus similar methods to those described herein can be used to extract ethanol from an aqueous mixture, including a fermentation mixture that produces ethanol from biomass materials such as those described herein. As described for acetic acid, fermentation can be conducted in the presence of DEB or other extraction liquids described herein as a separate phase, which extracts ethanol as it is produced so the ethanol production is not inhibited by build-up of product in the aqueous phase. Continuous processing of fermentation reactions can thus be achieved by contacting the fermentation reaction mixture with an extraction liquid such as DEB, and using the extraction liquid as a mechanism to conduct ethanol away from the fermentation without interrupting the fermentation reaction. The extraction liquid can be brought into contact with the fermentation reaction mixture and separated from it after at least some ethanol moves into the extraction liquid phase, either in batches or in a continuous process, permitting faster and more complete fermentation.

Distribution of isobutanol between extraction liquid and water is more favorable than distribution of either ethanol or acetic acid, i.e., the concentration of isobutanol in DEB is 2-3 times higher than the concentration of isobutanol in water when the DEB and water phases are in equilibrium. Thus isobutanol can be removed from or extracted from an aqueous mixture or fermentation broth like ethanol, but with greater efficiency. As described above for ethanol, an extraction liquid can thus be used to promote isobutanol production in a bioreactor by either batch-wise (periodic) extractions or by a continuous extraction process.

In another aspect, the invention provides a method for continuous extraction of acetic acid, ethanol, and/or isobutanol from an aqueous mixture. The method comprises contacting the aqueous mixture with extraction liquid to form a biphasic mixture. Once some of the polar organic (acetic acid, ethanol, isobutanol) has migrated into the extraction liquid phase, part of the extraction liquid phase is removed and more extraction liquid is added. The removal of extraction liquid can be done in portions or it can be done continuously. Methods for performing such continuous extractions are known in the art. In some embodiments, additional extraction liquid is added into the aqueous mixture so that it extracts some of the organic substance before it joins with the extraction liquid phase. For example, since the aqueous layer is more dense and thus below the extraction liquid phase, additional extraction liquid can be added into the aqueous layer, and as it moves upward through the aqueous layer, some of the polar organic substance migrates into the added extraction liquid. Because the extraction liquid phase rises to the top of the aqueous mixture, part of the extraction liquid can be removed from the top of the mixture, e.g., by permitting it to overflow into a collection system. In some embodiments, the collected extraction liquid solution containing the polar organic substance can be treated to remove the polar organic substance, allowing the extraction liquid to be reused in a continuous cyclic process. This permits a relatively small volume of extraction liquid to remove the polar organic substance from a larger aqueous mixture volume.

EXAMPLES

Example 1

Extraction of Acetic Acid from Water with DEB

1. Preparation of Acetic Acid Water Solution.

In three different vials 7.5 wt %, 3 wt % and 1.5 wt % of acetic acid solutions (in water) were prepared gravimetrically. The solution was mixed thoroughly to ensure homogeneity. All the preparations were done under ambient conditions.

2. Water Solubility in DEB.

The amount of water present in DEB was measured using a Karl-Fischer apparatus (Mettler-Toledo). In a typical measurement, in a vial, 0.1 g of water and 10 g of DEB was taken and were stirred to ensure good mixing. The vial was closed tightly and the solution was kept at room temperature for 5 hours to attain equilibrium. A small of amount of sample solution was withdrawn to test the water content using a Karl-Fischer apparatus. The water content was less than 300 ppm. In addition, when we added more water two phases were obtained; bottom water-rich phase and upper DEB-rich phase. This indicated that we already achieved a good phase separation.

To test the solubility of DEB in water, visual cloud-point method was adopted. In this trial experiment, about 10 gm of water was taken in a vial and slowly very small drops of DEB (0.0001 g) was added until cloud-point was reached. When the solution becomes cloud it implies the start of two phases. In this way, we found the DEB solubility in water to be less than 10 ppm.

The low solubility of DEB in water is further confirmed using COSMO-RS method. COSMO-RS is a novel quantum-chemical based program which, independent of experiments, predicts the thermodynamic properties of fluid mixtures. An important thermodynamic property which indicates the solubility is activity coefficient at infinite dilution, $\gamma_\infty$. Table 1 shows calculated results for acetic acid in water phase and in DEB phase. High $\gamma_\infty$ (>5) means weaker interactions (or very low solubility) between the solute and solvent.

At 25° C., COSMO-RS predicted activity coefficient ($\gamma_\infty$) of water in DEB is 8.1, whereas for DEB in water, $\gamma_\infty$ is 16100. This value indicates non-ideality of DEB-water solutions and is commonly seen for longer chain hydrocarbons and aromatics that are nearly insoluble in water.

3. Solubility of Acetic Acid in DEB.

Pure glacial acetic (99% purity, Fischer Scientific) was weighed gravimetrically and was dissolved in DEB. We were able to dissolve 30 wt % of glacial acetic acid in DEB. The solubility measurements were confirmed through visual observation and also by using GC and ATR-IR. Furthermore, $\gamma_\infty$, as predicted from COSMO-RS for acetic acid in DEB at room temperature is very low (0.31). This lower value of indicates high solubility of acetic acid in DEB.

4. Distribution of Acetic Acid Between Aqueous and DEB Phases.

To measure the distribution of acetic acid between the DEB and water phase, contact experiments were performed. To the previously prepared different known weight fractions of acetic acid in water (7.5 wt %, 3 wt % and 1.5 wt % acetic acid and range of mass fraction is 7-11.5 wt %), a known amount of DEB (solvent to feed ratio was approximately 1:1 mass ratio) was added. The prepared solutions were vortexed (3000 rpm) for 5 minutes. Then the samples were allowed to phase equilibrated for 12 h. Once the equilibrium reached the two phases were separated carefully and their volume and mass were measured precisely. This was done to calculate the density of the both DEB and water rich phases. In addition, material balances of both phases were also determined.

The water contents in both phases were measured using a Karl-Fischer apparatus. In the DEB phase, water content was less than 300 ppm. This shows very little migration of water into the DEB phase.

Acetic acid in the water phase was measured using HPLC (Shimadzu, R I). The amount of acetic acid in the DEB phase was measured using GC (Varian) and ATR-IR. In the case of ATR-IR, acetic acid shows absorption at 1725-1750 cm$^{-1}$ wave numbers in the IR region, whereas DEB does not show any absorption in this region. This is a good way to test the solubility of acetic acid in DEB. A calibration curved was prepared for IR for acetic acid measurements. All the measurement errors were below ±2%.

Table 1 describes the distribution of acetic acid between water and DEB phases as measured at 25° C. for a single extraction step. Table 1 also gives amounts of water in the DEB phase, measured in micrograms. In each case, good phase separation was observed, and the aqueous phase was more dense than the DEB phase.

TABLE 1

Extraction results for acetic acid in water phase and in DEB phase (amounts are in grams unless otherwise indicated).

| Amount of DEB | Amount of AcOH (initially in water) | Amount of water | AcOH in water (final in DEB) | AcOH in DEB | Water in DEB (µg) | D = AcOH in DEB/AcOH in water | Distribution Coefficient |
|---|---|---|---|---|---|---|---|
| 4.91 | 0.33 | 4.1 | 0.163 | 0.171 | 300 | 1.1 | 0.91 |
| 5.8 | 0.17 | 4.2 | 0.082 | 0.088 | 100 | 1.08 | 0.78 |
| 6.5 | 0.07 | 4.3 | 0.034 | 0.033 | 90 | 0.98 | 0.65 |

Example 2

Distribution of Ethanol and Isobutanol Between Water and DEB Phases

The amount of ethanol and isobutanol in water phase was measured using HPLC (see above for details). The concentrations of ethanol taken were: 8, 6, 3, 2, 1 and 0.5 wt %.

Table 2 provides the distribution coefficient of ethanol between water and DEB phase. Distribution coefficient is reported on the basis of HPLC results of aqueous phase and that of mass balance of both the phases. Experiments are currently underway to determine the amount of ethanol, iso butanol in DEB phase. Gas chromatography will be used to quantify the amount of ethanol and isobutanol present in the DEB phase. Water measurements will be done using a Karl Fischer apparatus.

The distribution coefficient for all these concentrations is between 0.9-1.2. This is similar to that of acetic acid.

TABLE 2

Distribution of ethanol between water and DEB phase. Results are provided for a single extraction step; all amounts are in grams unless otherwise specified.

| Amount of DEB (g) | Amount of EtOH (initially in water) | Amount of water | Amount of EtOH in water (final) | Amount of EtOH in DEB (final) | D = conc. of EtOH in DEB/ conc. of EtOH in water |
|---|---|---|---|---|---|
| 4.63 | 0.99 | 4.62 | 0.51 | 0.48 | 0.94 |
| 4.71 | 0.31 | 4.70 | 0.15 | 0.16 | 1.06 |
| 4.85 | 0.16 | 4.86 | 0.073 | 0.087 | 1.2 |
| 4.92 | 0.11 | 4.89 | 0.052 | 0.058 | 1.11 |
| 4.97 | 0.06 | 4.98 | 0.031 | 0.029 | 0.93 |
| 5.02 | 0.03 | 5.03 | 0.014 | 0.016 | 1.16 |

Table 3 provides distribution coefficient for isobutanol between water and DEB phase. Here also, distribution coefficient is reported on the basis of HPLC results of aqueous phase and that of mass balance of both the phase.

TABLE 3

Distribution of isobutanol between water and DEB phase. All the masses are expressed in grams. Results are provided for single extraction step.

| Amount of DEB (g) | Amount of iBuOH (initially in water) | Amount of water | Amount of iBuOH in water (final) | Amount of iBuOH in DEB (final) | D = conc. of EtOH in DEB/ conc. of ETOH in water |
|---|---|---|---|---|---|
| 4.76 | 0.26 | 4.74 | 0.07 | 0.19 | 2.71 |
| 4.88 | 0.13 | 4.89 | 0.03 | 0.10 | 3.33 |
| 4.93 | 0.071 | 4.92 | 0.018 | 0.053 | 2.72 |
| 5.08 | 0.028 | 5.03 | 0.0061 | 0.0219 | 3.59 |

High distribution coefficients are obtained for 5, 3, 2, and 1 wt % of isobutanol. In this case, the measured distribution coefficients for all of the above concentrations are between 2.5-3.5, which is higher in comparison to the distribution coefficients for acetic acid and ethanol. This shows the enhanced recovery of isobutanol by using diethylene glycol dibutyl ether as an extraction solvent.

Example 3

Correlation with Theoretical Estimations of Solvent/Solute Interactions

Modeling of the interactions between DEB, water, and selected small, polar organic compounds were consistent with the above experimental observations. A novel quantum chemical based modeling program, COSMO-RS, predicts thermodynamic properties of fluid mixtures. COSMO-RS is a product of COSMOlogic GmbH & Co. KG. It was used to predict activity coefficients at infinite dilution ($\gamma_\infty$) for water in DEB, at various temperatures. It shows water has a low affinity for DEB. Similarly, predictions of $\gamma_\infty$ for DEB in water show DEB has a low affinity for water (Table 5). Finally, predictions for acetic acid in DEB show that acetic acid should dissolve relatively well in DEB (Table 6), and that solubility of acetic acid in DEB should increase with increasing temperature. The models demonstrate that the amount of water dissolving in DEB and the amount of DEB dissolved in water should decrease at higher temperatures. This means operating at higher temperatures will further enhance the immiscibility gap of the DEB-water system, improving upon the already-desirable properties these extraction liquids provide.

TABLE 4

COSMO-RS predicted activity coefficient at infinite dilution for water in DEB as a function of temperature.
Alcohol Type $\gamma_\infty$

| $\gamma_\infty$ | Temperature (° C.) |
|---|---|
| 4.93 | 25 |
| 5.05 | 35 |
| 5.10 | 45 |
| 5.12 | 55 |
| 5.14 | 65 |
| 5.15 | 75 |

TABLE 5

COSMO-RS predicted activity coefficient at infinite dilution for DEB in water as a function of temperature.

| $\gamma_\infty$ | Temperature (° C.) |
|---|---|
| 167209 | 25 |
| 223462 | 35 |
| 278451 | 45 |
| 324811 | 55 |
| 355400 | 65 |
| 367691 | 75 |

TABLE 6

COSMO-RS predicted activity coefficient at infinite dilution for acetic acid in DEB as a function of temperature.
When $\gamma_\infty$ is near 1, the solution is nearly ideal.

| $\gamma_\infty$ | Temperature (° C.) |
|---|---|
| 0.32 | 25 |
| 0.38 | 35 |
| 0.46 | 45 |
| 0.55 | 55 |
| 0.63 | 65 |
| 0.72 | 75 |

TABLE 7

COSMO-RS calculated activity coefficient at infinite dilution ($\gamma_\infty$) for isomers of C2-C6 alcohols in DEB at 25° C. and for C2-C6 carboxylic acids in DEB at 25° C..

| Ethanol | 1.24 |
|---|---|
| 1-propanol | 1.21 |
| 2-propanol | 1.11 |
| 1-butanol | 1.02 |
| 2-butanol | 0.91 |
| Isobutanol | 0.81 |
| t-butanol | 0.62 |
| 1-pentanol | 0.82 |
| 2-pentanol | 0.56 |
| 2-methyl-2-butanol | 0.73 |
| 1-hexanol | 0.74 |
| 2-hexanol | 0.63 |
| 2-methyl-2-pentanol | 0.59 |

| Carboxylic acid type | $\gamma_\infty$ |
|---|---|
| Acetic acid | 0.31 |
| Propanoic acid | 0.32 |
| Butyric acid | 0.16 |
| Valeric acid | 0.17 |
| n-hexanoic acid | 0.14 |

The amounts of hydroxymethylfurfural and furfural in water phase were measured

| Carboxylic acid type | $\gamma_\infty$ |
|---|---|
| Acetic acid | 0.31 |
| Propanoic acid | 0.32 |
| Butyric acid | 0.16 |
| Valeric acid | 0.17 |
| n-hexanoic acid | 0.14 | using HPLC (see above for details). Table 8 provides the distribution coefficient of hydroxymethylfurfural (HMF) between water and DEB phase. Distribution coefficient is reported on the basis of HPLC results of aqueous phase and that of mass balance of both the phases. The amount of hydroxymethylfurfural in DEB phase may be quantified using gas chromatography. Water measurements of the separated DEB phase containing hydroxymethylfurfural may be carried out using a Karl Fischer apparatus.

TABLE 8

Distribution of hydroxymethylfurfural (HMF) between water and DEB phase at 25° C. All masses are expressed in grams. Results are provided for a single extraction step.

| Amount of DEB (g) | Amount of HMF (g) (initial in water phase) | Amount of water (g) | Amount of HMF in water phase (g) (final) | Amount of HMF in DEB phase (g) (final in DEB phase) | D = conc. of HMF in DEB/conc. of HMF in water |
|---|---|---|---|---|---|
| 5.01 | 0.0512 | 5.11 | 0.0321 | 0.0191 | 0.59 |
| 5.02 | 0.0251 | 5.03 | 0.0161 | 0.0088 | 0.54 |
| 5.01 | 0.0132 | 5.01 | 0.0083 | 0.0050 | 0.61 |

Table 9 provides distribution coefficient for furfural between water and DEB phase. Distribution coefficient is reported on the basis of HPLC results of aqueous phase and that of mass balance of both the phases. The amount of furfural in DEB phase may be quantified using gas chromatography. Water measurements of the separated DEB phase containing furfural may be carried out using a Karl Fischer apparatus.

TABLE 9

Distribution of furfural between water and DEB phase at 25° C. All masses are expressed in grams. Results are provided for a single extraction step.

| Amount of DEB (g) | Amount of furfural (g) (initial in water phase) | Amount of water (g) | Amount of furfural in water phase (g) (final) | Amount of furfural in DEB phase (g) (final in DEB phase) | D = conc. of furfural in DEB/conc. of furfural in water |
|---|---|---|---|---|---|
| 4.98 | 0.0491 | 5.01 | 0.0249 | 0.0242 | 0.98 |
| 5.02 | 0.0242 | 4.98 | 0.0161 | 0.0088 | 0.91 |
| 5.11 | 0.0141 | 5.05 | 0.0069 | 0.0071 | 1.03 |

The invention claimed is:

1. A method to extract one or more organic compounds from an aqueous mixture, comprising contacting the aqueous mixture with an extraction liquid of Formula I, II or III:

(I)

(II)

(III)

wherein each R and R' is independently C3-C5 alkyl, and each R" is independently selected from C3-C5 alkyl and C3-C5 acyl, to produce a biphasic composition;

and separating at least a portion of the extraction liquid phase from the aqueous phase to provide an extract solution comprising the organic compound.

2. The method of claim 1, wherein the organic compound is a C2-C6 monohydric alcohol, a C2-C6 carboxylic acid, or a C2-C6 aldehyde or ketone.

3. The method of claim 1, wherein the organic compound is selected from the group consisting of acetic acid, propionic acid, butyric acid, valeric acid, hexanoic acid, hydroxypropionic acid, hydroxybutyric acid, ethanol, propanol, isopropanol, 1-butanol, 2-butanol, isobutanol, t-butanol, 1-pentanol, 2-pentanol, 2-methyl-2-pentanol, 1-hexanol, 2-hexanol, and 2-methyl-2-pentanol.

4. The method of claim 1, wherein the aqueous mixture is a fermentation broth or partially processed fermentation broth.

5. The method of claim 1, wherein the organic compound is ethanol, acetic acid, 1-butanol, or isobutanol.

6. The method of claim 5, wherein the organic compound is acetic acid, and wherein the aqueous mixture has a pH of about 9 or less.

7. The method of claim 1, wherein the extraction liquid comprises a compound of Formula I.

8. The method of claim 7, wherein the extraction liquid is a compound of Formula I, and wherein all of the R groups are the same.

9. The method of claim 8, wherein the extraction liquid is diethylene glycol dibutyl ether (DEB).

10. The method of claim 8, wherein the extraction liquid is diethylene glycol diisobutyl ether.

11. The method of claim 1, wherein the extraction liquid comprises a compound of Formula II.

12. The method of claim 1, wherein the extraction liquid comprises a compound of Formula III.

13. The method of claim 12, wherein the extraction liquid comprises tripropionin.

14. The method of claim 1, wherein the organic compound is acetic acid, and wherein the acetic acid is extracted from the aqueous mixture with a distribution coefficient of about 0.5 to about 1.0.

15. The method of claim 1, wherein the organic compound is ethanol, and wherein the ethanol is extracted from the aqueous mixture with a distribution coefficient of about 0.8 to about 1.4.

16. The method of claim 1, wherein the organic compound is isobutanol, and wherein the isobutanol is extracted from the aqueous mixture with a distribution coefficient of about 2.3 to about 4.1.

17. The method of claim 1, wherein the organic compound is hydroxymethylfurfural.

18. The method of claim 17, wherein the hydroxymethylfurfural is extracted from the aqueous mixture with a distribution coefficient of about 0.4 to about 0.7.

19. The method of claim 1, wherein the organic compound is furfural.

20. The method of claim 19, wherein the furfural is extracted from the aqueous mixture with a distribution coefficient of about 0.8 to about 1.2.

* * * * *

UNITED STATES PATENT AND TRADEMARK OFFICE
CERTIFICATE OF CORRECTION

PATENT NO. : 8,835,660 B2
APPLICATION NO. : 13/818624
DATED : September 16, 2014
INVENTOR(S) : Amit A. Gokhale et al.

It is certified that error appears in the above-identified patent and that said Letters Patent is hereby corrected as shown below:

On the Title Page, Item (56) under OTHER PUBLICATIONS, in column 2, line number 4, delete "recived" and insert --received--, therefor.

Signed and Sealed this
Fourteenth Day of April, 2015

Michelle K. Lee
*Director of the United States Patent and Trademark Office*